United States Patent
Sommercorn et al.

(10) Patent No.: US 6,494,848 B1
(45) Date of Patent: Dec. 17, 2002

(54) MEASURING DEVICE FOR USE WITH A HEMOSTATIC PUNCTURE CLOSURE DEVICE

(75) Inventors: Richard Kay Sommercorn, Renton; Richard Dale Allison, Woodinville, both of WA (US)

(73) Assignee: St. Jude Medical Puerto Rico B.V., Amsterdam (NL)

( * ) Notice: Subject to any disclaimer, the term of this patent is extended or adjusted under 35 U.S.C. 154(b) by 0 days.

(21) Appl. No.: 08/990,668

(22) Filed: Dec. 15, 1997

Related U.S. Application Data
(60) Provisional application No. 60/034,266, filed on Dec. 19, 1996.

(51) Int. Cl.[7] .............................................. A61B 5/103
(52) U.S. Cl. ........................... 600/587; 33/512; 33/700; 606/191
(58) Field of Search .......................... 600/587; 606/191, 606/194; 33/511, 512, 700

(56) References Cited

U.S. PATENT DOCUMENTS

| | | | | |
|---|---|---|---|---|
| 4,224,951 A | * | 9/1980 | Hasson | 600/591 |
| 4,293,962 A | | 10/1981 | Fuson | 3/1.9 |
| 4,744,364 A | | 5/1988 | Kensey | 128/334 R |
| 4,852,568 A | | 8/1989 | Kensey | 128/325 |
| 4,890,612 A | | 1/1990 | Kensey | 606/213 |
| 5,013,318 A | * | 5/1991 | Spranza, III | 606/102 |
| 5,108,421 A | | 4/1992 | Fowler et al. | 606/213 |
| 5,171,248 A | * | 12/1992 | Ellis | 606/102 |
| 5,197,465 A | * | 3/1993 | Montgomery | 128/207.29 |
| 5,292,309 A | | 3/1994 | Van Tassel et al. | 604/117 |
| 5,383,896 A | * | 1/1995 | Gershony et al. | 606/213 |
| 5,391,183 A | | 2/1995 | Janzen et al. | 606/213 |
| 5,411,520 A | | 5/1995 | Nash et al. | 606/213 |
| 5,413,571 A | | 5/1995 | Katsaros et al. | 606/213 |
| 5,419,765 A | | 5/1995 | Weldon et al. | 604/96 |
| 5,431,639 A | * | 7/1995 | Shaw | 604/11 |
| 5,507,744 A | * | 4/1996 | Tay et al. | 606/50 |
| 5,645,566 A | * | 7/1997 | Brenneman et al. | 604/174 |
| 5,728,134 A | * | 3/1998 | Barak | 606/214 |
| 5,810,810 A | * | 9/1998 | Tay et al. | 606/50 |

* cited by examiner

Primary Examiner—Cary O'Connor
Assistant Examiner—Charles Marmor, II
(74) Attorney, Agent, or Firm—Dorsey & Whitney LLP

(57) ABSTRACT

A measuring device is disclosed which includes a proximal end portion having an actuation member thereon and a distal end portion having an expandable member thereon wherein the actuation member and the expandable member are in mechanical or fluid communication via a lumen which extends therebetween such that actuation of the actuation member causes the radial expansion of the expansion member so that when the measuring device is placed in a puncture with the distal end portion in a blood vessel, the measuring device may be withdrawn until the expandable member contacts the wall of the blood vessel adjacent to the puncture to provide the user with an indication of the distance between and/or depth of the blood vessel beneath the skin of the patient.

20 Claims, 5 Drawing Sheets

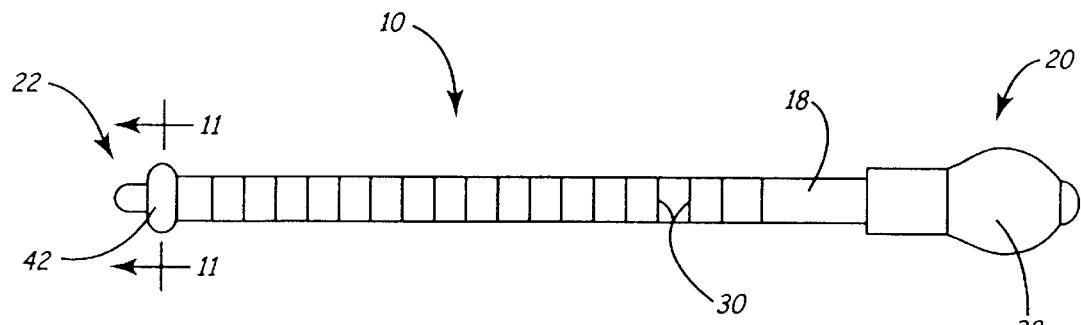
FIG. 8
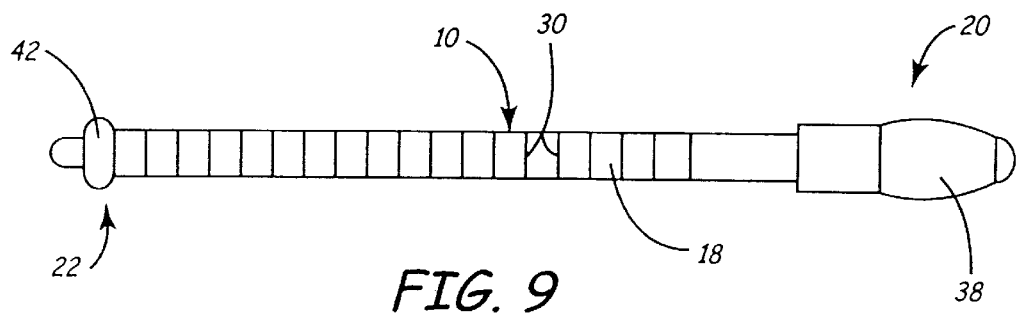
FIG. 9
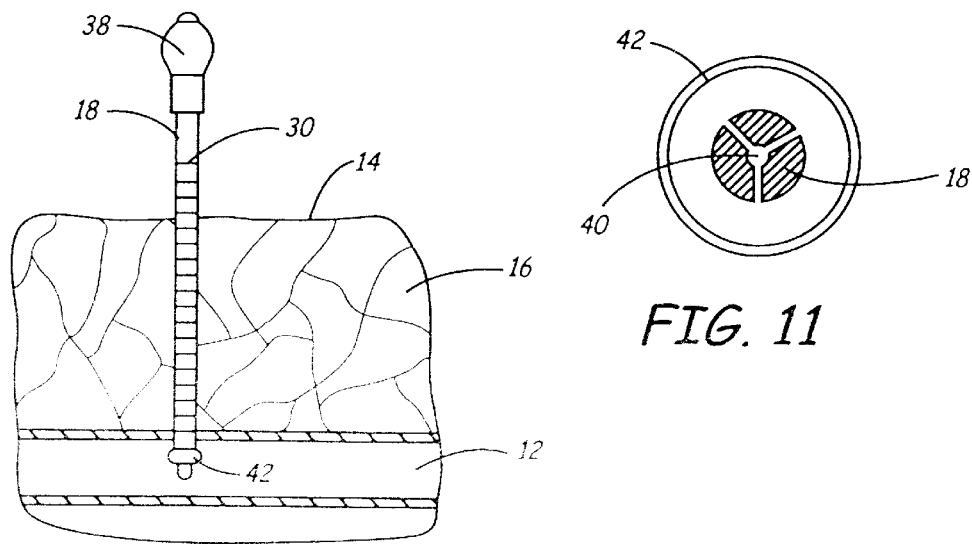
FIG. 10
FIG. 11

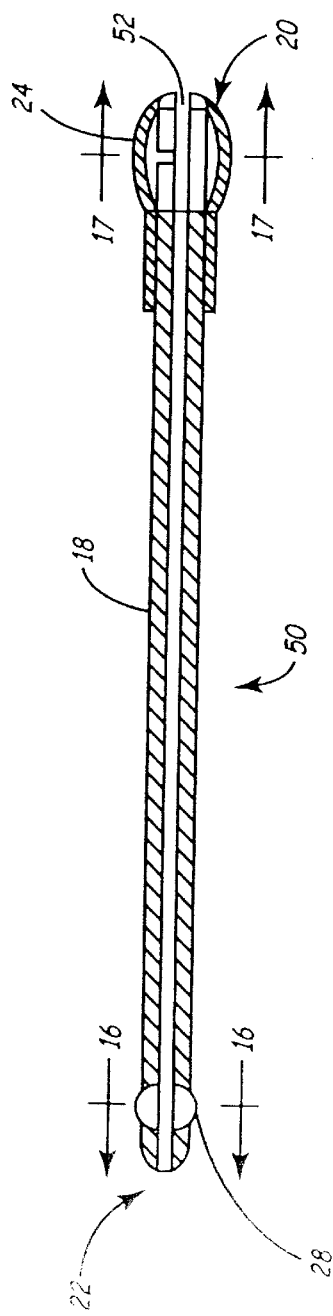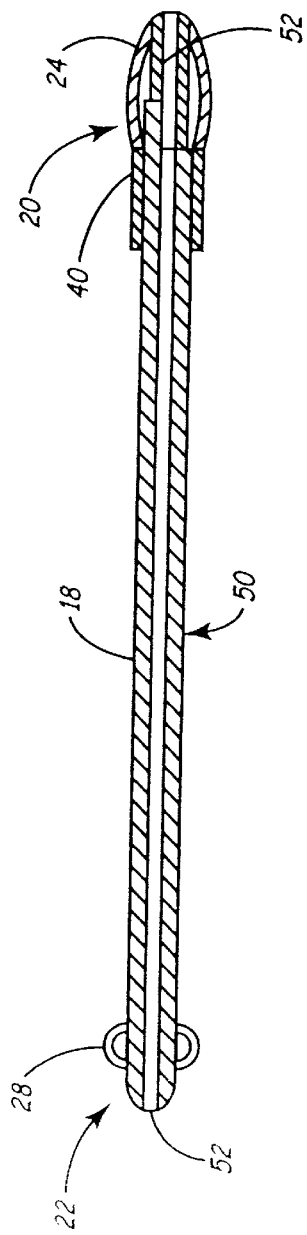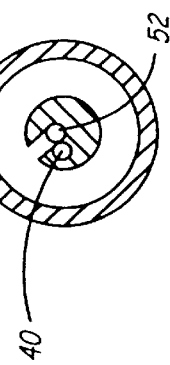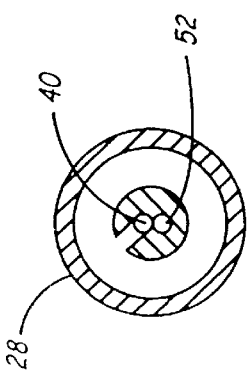
FIG. 14
FIG. 15
FIG. 16
FIG. 17

MEASURING DEVICE FOR USE WITH A HEMOSTATIC PUNCTURE CLOSURE DEVICE

This application claims benefit of provisional application 60/034,266 filed Dec. 19, 1996.

FIELD OF THE INVENTION

The present invention generally relates to a surgical instrument used during a catheterization procedure, and more particularly to an instrument for accurately measuring the depth below the skin surface to a blood vessel, duct or target organ through which the catheter is to be passed. Even more particularly, one form of the present invention is adapted for use prior to the placement of a vascular hemostasis device to accurately determine the desired size and length of the hemostasis device to seal the puncture or incision.

BACKGROUND OF THE INVENTION

During catheterization procedures, the nurse or physician will create an opening into an artery or other vessel with a conventional catheter introducer or dilator. In a typical interventional procedure, such as the placement of a vascular catheter, the Seldinger technique is used to gain access to the blood vessel. Initially, a needle trocar is passed through the skin to puncture an opening through the wall of an artery. Next, a dilator may be passed over the trocar to enlarge the diameter of the puncture wound so that it can accommodate an introducer. Once the introducer is positioned in the puncture, a guidewire is inserted through the introducer. Finally, the introducer is removed and the catheter is advanced over the guidewire and into the blood vessel of the patient.

The size of the opening will vary depending on the type of procedure and the size of the catheter which is used. For example, the diameter of the catheter and catheter sheath used in standard angiography procedures is typically between 5 to 8 French (1.67 mm and 2.67 mm, respectively). The diameter of the catheter and catheter sheath used in angioplasty procedures may be 8 (2.67 mm) or 9 (3.33 mm) French. The diameter of the catheter and catheter sheath used in intro-aortic balloon pump procedures is typically between 14 to 16 French (4.67 mm and 5.33 mm, respectively) and the diameter of the catheter and catheter sheath used with cardiopulmonary support systems is typically between 18 and 20 French (6.0 mm and 6.67 mm, respectively). Additionally, the catheter is often twisted or otherwise manipulated as it is advanced to the treatment site, thereby causing a further enlargement of the incision or puncture in the body of the patient.

When the medical procedure is completed and the catheter is removed from the artery or other blood vessel, conventional practice has been to apply external pressure to the entry site until clotting occurs. Because many of the patients undergoing these procedures have been medicated with an anticoagulant such as heparin, the nurse may be required to apply external pressure to the incision site for an extended period of time. The time required to stop bleeding at the incision site is not an efficient use of the nurses time and a painful hematoma or unsightly bruise may still occur at the incision site because the artery will continue to bleed internally until clotting blocks the opening in the artery.

One approach to resolving the problem of sealing the puncture or incision is disclosed in U.S. Pat. No. 4,744,364 granted to Kensey on May 17, 1988, and related U.S. Pat. Nos. 4,852,568 and 4,890,612 granted to Kensey on Aug. 1, 1989, and Jan. 2, 1990, respectively. The first two Kensey patents disclose a device for sealing an opening in the wall of a blood vessel which consists of an elongate tubular body having an anchor member removably disposed therein. The tubular body also includes an ejecting device disposed within the tubular body for forcing the anchor member from the tubular body into the interior of the blood vessel. A retraction suture is secured to the anchor member so that the engagement surface of the anchor member hemostatically engages the inner surface of the blood vessel contiguous with the puncture. The '612 Kensey patent discloses a device which includes an elongate member having a portion thereof which is adapted to engage portions of the tissue adjacent to the punctured vessel and a sealing portion which extends through the incision to engage the tissue contiguous therewith to seal the puncture. Subsequent patents granted to Kensey et al. are illustrative of improvements to the basic approach described above and generally include an anchor member which is used in combination with a suture and a collagen member to seal an incision and blood vessel.

U.S. Pat. No. 5,411,520 granted to Nash et al. is illustrative of an improvement to the basic approach described above and generally includes a spacer which is movable along a suture to position the spacer between the anchor member and the collagen member to seal the puncture and blood vessel. The spacer is positioned between the collagen member and the anchor to prevent the collagen member from being entering the blood vessel of the patient.

U.S. Pat. No. 5,108,421 granted to Fowler, and assigned to the assignee of the present invention, discloses the use of a "vessel plug" type approach wherein the hemostatic closure device is inserted into the incision of the patient and may be positioned in the incision using a locating member such as an elongate balloon type member or a syringe type device. U.S. Pat. No. 5,391,183 granted to Janzen et al. discloses another vessel plug type approach wherein one or more oversized vessel plugs are inserted into the incision using a device with a plunger member.

An important consideration in each of the sealing devices described above, is to accurately identify the location of the blood vessel below the access sheath or skin surface of the patient. This is particularly true for the "vessel plug" types of sealing devices because the collagen plug is intended to be positioned in contact with the outer surface of the wall of the blood vessel without extending into the blood vessel. To accomplish this, it is important to accurately determine the depth of the puncture and accurately position the delivery device for the collagen plug. It is also desirable to apply a sufficient amount of hemostasis promoting material into the puncture so that the bleeding from the blood vessel is rapidly and securely stopped.

SUMMARY OF THE INVENTION

It is accordingly an object of the present invention to provide a measuring device for use with hemostatic closure devices for accurately assessing the depth of the blood vessel beneath the skin of the patient.

It is yet another object of the present invention to provide a measuring device which is simple to use and manufacture and which provides an accurate and reproducible measurement.

In one form of the present invention, the measuring device includes an elongate tubular member having a proximal end, a distal end and a lumen extending therebetween. The distal end portion of the elongate member is preferably rounded and includes a radially expandable member spaced slightly behind the distal end. The expandable member is preferably in communication with a proximally located actuation member via the lumen. The proximal end of the elongate member preferably includes a deformable member, such as a squeeze bulb or disk member on the proximal end of the elongate member. The deformable member may be mechanically or fluidly interconnected with the expandable member by using a wire which extends the length of the measuring device or using fluid pressure to expand the expandable member. The outer circumference of the elongate member preferably includes markings thereon to provide the user with an indication of the depth of the expandable member relative to the proximal end of the access heath or skin of the patient. The markings may include graduations, bands, stripes or other visually observable indicia. In use, the measuring device is inserted in a conventional manner, such as through a procedure sheath or tear apart sheath, and into the puncture once the procedure has been completed. The user may then squeeze the actuation member on the proximal end of the measuring device to cause the expansion of the bulb-type member on the distal end thereof. The user may then withdraw the measuring device in the puncture until resistance is felt. The existence of resistance to the withdrawal of the measuring device is indicative that the expandable member has contacted the wall of the blood vessel adjacent to the puncture. The user may then view the markings on the exterior of the measuring device and note the depth of the puncture. The appropriate hemostasis or other device may then be selected according to the determined depth and the puncture may be sealed using one of the commercially available hemostasis devices.

In accordance with another form of the present invention, the elongate member may include a further lumen therein to allow the measuring device to be passed over a guidewire during insertion of the measuring device into the puncture.

The present invention may also be modified to include a slidable member, such as a marking ring, on the outer surface of the measuring device so that once the location of the blood vessel is determined, the slidable member may be moved into contact with the skin of the patient. The measuring device may then be removed from the puncture and the user may choose the appropriate sealing device by observing the depth indicated by the position of the slidable member on the measuring device.

An advantage of the present invention is that it is simple to manufacture and use.

A further advantage of the present invention is that it may be used in nearly any medical procedure where it is desirable to accurately and consistently identify the depth of a puncture for sheath placement or for subsequent insertion of a medical device such as a hemostatic puncture closure device or sealing device.

DESCRIPTION OF THE DRAWINGS

FIG. 8 is a partially elevated side view showing an alternate preferred form of the present invention;

FIG. 9 is an enlarged side elevational view showing the alternate preferred form of FIG. 8 with the distal end portion of the measuring device in the expanded condition;

FIG. 10 is an enlarged side view showing the alternate preferred form of FIG. 8 positioned in a puncture in a patient to measure and identify the depth and location of the blood vessel of the patient beneath the skin surface;

FIG. 11 is a cross-sectional view of the alternate preferred embodiment shown in FIG. 8 taken generally along lines 11—11 of FIG. 8;

FIG. 14 is an elevated side view, partially in cross-section showing an alternate form of the present invention;

FIG. 15 is an elevated side view, partially in cross-section showing the alternate embodiment of the present invention shown in FIG. 14;

FIG. 16 is a cross-sectional view of the alternate embodiment of the present invention shown in FIG. 14 taken generally along lines 16—16 of FIG. 14;

FIG. 17 is a cross-sectional view of the alternate embodiment of the present invention shown in FIG. 14 taken generally along lines 17—17 of FIG. 14.

DETAILED DESCRIPTION OF THE PRESENT INVENTION

Figure 1:
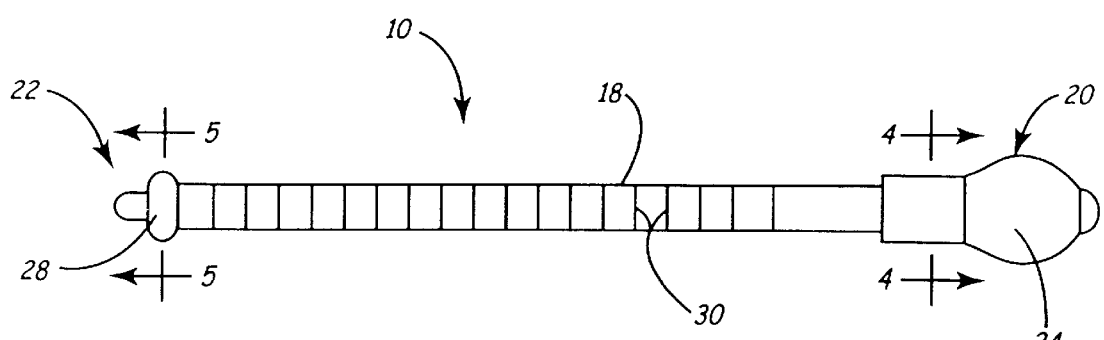
FIG. 1 is a partially elevated side view showing the preferred form of the present invention.
Figure 2:
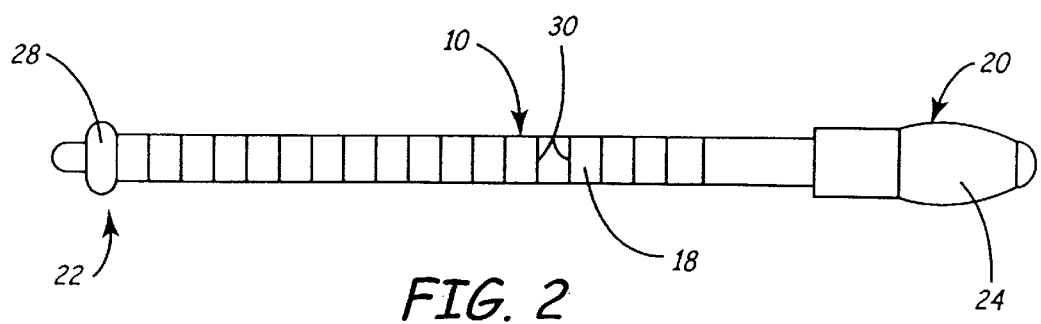
FIG. 2 is an enlarged side elevational view showing the preferred form of the present invention with the distal end portion of the measuring device in the expanded condition.
Figure 3:
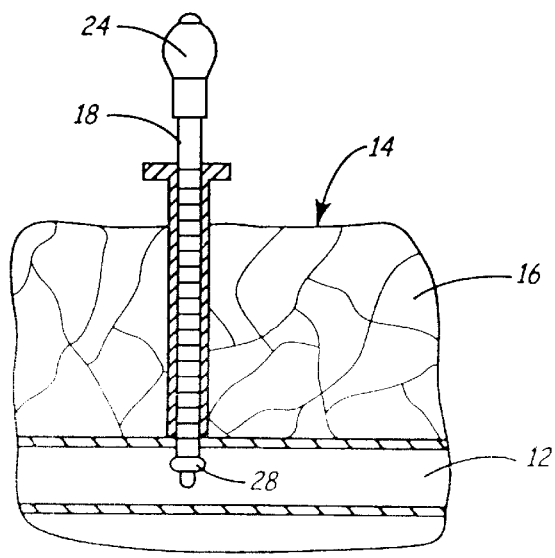
FIG. 3 is an enlarged side view showing the preferred form of the present invention inserted in a procedure sheath and located within a puncture in a patient to identify the depth and location of the blood vessel of the patient beneath the skin surface.
Figure 4:
FIG. 4 is a cross-sectional view of the preferred embodiment of the present invention shown in FIG. 1 taken generally along lines 4—4 of FIG. 1.
Figure 5:
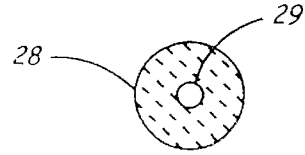
FIG. 5 is a cross-sectional view of the preferred embodiment of the present invention shown in FIG. 1 taken generally along lines 5—5 of FIG. 1.
Figure 6:
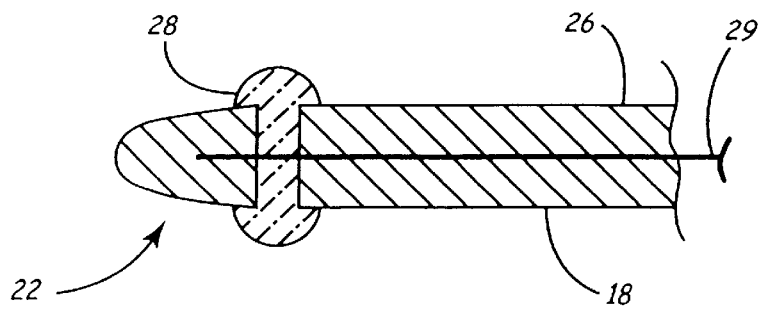
FIG. 6 is a cross-sectional view of the distal end portion of the preferred embodiment of the present invention shown in FIG. 1.
Figure 7:
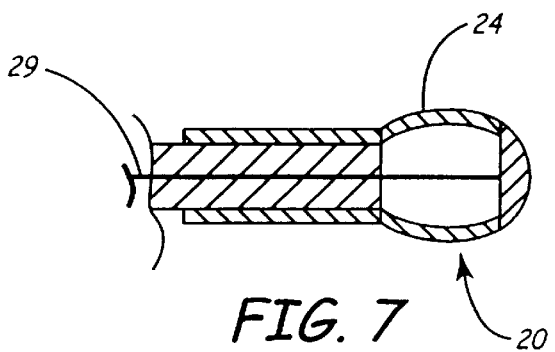
FIG. 7 is a cross-sectional view of the proximal end portion of the preferred embodiment of the present invention shown in FIG. 1.
Figure 12:
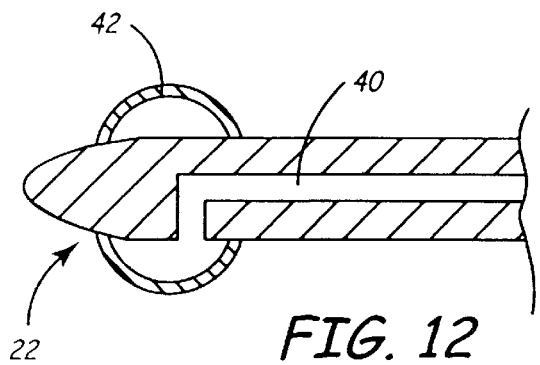
FIG. 12 is a cross-sectional view of the distal end portion of the preferred embodiment of the present invention shown in FIG. 8.
Figure 13:
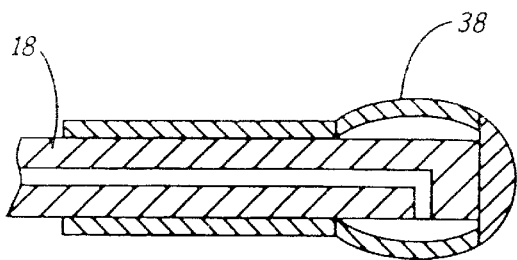
FIG. 13 is a cross-sectional view of the proximal end portion of the preferred embodiment of the present invention shown in FIG. 8.

The present invention is described hereinafter with specific reference to the use of the present invention for measuring the depth of a puncture or incision and then subsequently sealing an incision or puncture in a blood vessel such as the femoral artery 12 of a patient. As shown in the preferred use of the present invention, the measuring device 10 is intended to measure the depth of the puncture or incision from the access sheath or the skin 14 of the patient, through subcutaneous tissue, such as adipose tissue 16 and into a blood vessel or target organ. Despite the preferred use described herein, it is contemplated that the present invention may be used with nearly any catheterization or other medical procedure wherein it is desirable to accurately measure or identify the depth of a puncture or incision. For example, the present invention may be used to reliably and accurately position the distal end of a procedure sheath adjacent to the wall of the blood vessel or target organ. Additionally, the present invention may be used to accurately position a suture type of puncture sealing device along or adjacent to the wall of a blood vessel or select the appropriate size of sealing device to be used.

As used herein, the distal end of the measuring device 10 or an element is referred to as the end of the element nearest to the patient and the proximal end of the measuring device 10 or an element is referred to as the element furthest away from the patient.

As shown in FIGS. 1–7, one form of the measuring device 10 of the present invention generally consists of a semi-rigid and elongate tubular body portion 18 having a proximal end portion 20 and a distal end portion 22. The proximal end portion 20 preferably includes an actuation member 24, such as a deformable member or squeeze bulb which is in mechanical communication with the proximal end portion 20 of the measuring device via a wire 29 which is slidably contained in a lumen 26 that extends lengthwise through the body portion 18 of the measuring device. The distal end portion 22 of the measuring device is preferably slightly rounded to allow for the atraumatic insertion thereof and includes a radially expandable member 28 thereon. The distal end portion 22 of the measuring device is also preferably movable with respect to the remainder of the measuring device in response to the movement of the wire 29. The wire 29 is preferably an elongate and flexible member which extends between and is preferably physically connected to the proximal end portion of the actuation member and the distal end portion 22 of the measuring device. The wire 29 merely provides tension to the distal end portion of the measuring device and therefore, may be constructed of nearly any material, so long as tension is applied therethrough to the distal end portion when the actuation member is actuated. The expandable member 28 is responsive to actuation of the actuation member 24 via the wire 29 such that compression of the actuation member 24 on the proximal end portion 20 of the measuring device causes the wire 29 in the lumen 26 to retract the distal tip of the measuring device relative to the remainder of the measuring device. This retraction of the wire 29 and proximal movement of the distal tip causes the radial expansion of the expandable member 28 on the distal end portion 22 of the measuring device 10 by compressing the expandable member 28 between the distal tip and distal end portions of the measuring device.

The radial size of the expandable member in the relaxed and expanded positions is preferably chosen so as to allow easy insertion through the puncture with or without the use of a procedure or tear apart sheath and so as to not significantly obstruct the flow of blood through the blood vessel during insertion or while in the expanded condition. The radial size is also preferably sufficient to provide the user with reliable tactile feedback to signal to the user that the expandable member 28 has contacted the wall of the blood vessel adjacent to the puncture. Additionally, the size of the expanded expandable member 28 is preferably sufficient to block the flow of blood from the blood vessel into the puncture once the expandable member is positioned in the desired location adjacent to the wall of the blood vessel and puncture.

The body portion 18 of the measuring device is preferably formed of a semi rigid material, such as a plastic which may be opaque or transparent and includes spaced apart markings 30 thereon. The lumen 26 is preferably as small as possible while still allowing the wire 29 to provide the mechanical communication between the actuation member 24 and expandable member 28. The diameter of the body portion is chosen so as to conform to the diameter restrictions imposed by the intended size of the puncture and the procedure sheath used during the prior medical procedure. As shown best in FIGS. 1 and 2, the markings 30 are printed or otherwise embossed on the outer surface of the body portion. The markings 30 begin proximally of the expandable member 28 to provide the user with an indication of the depth of the puncture relative to the interface of the proximal side of the expandable member 28 and the body portion 18. As shown, the markings 30 are preferably evenly spaced apart along the body portion 18 and may include colored bands, numbers or other readily observable indicators of the relative depth of the puncture.

In use, after the medical procedure has been performed, the user may insert the measuring device 10 into the puncture in a conventional manner through the procedure sheath while manual pressure is applied to the patient at a location above the puncture site to minimize the flow of blood through the puncture. Alternately and less preferably, the user may insert the measuring device through the puncture site without the use of the procedure sheath. Once the user confirms that the distal end portion 22 of the measuring device has entered the blood vessel, the user may release the manual pressure and squeeze or otherwise actuate the actuation member 24. Actuation of the actuation member 24 causes the wire 29 in the lumen 26 to move proximally in the lumen 26 and retract the distal tip on the distal end portion 22 of the measuring device. The proximal movement of the distal tip causes the radial expansion of the expandable member 28. Once the radial dimension of the expandable member has been expanded, the user may withdraw the measuring device 10 in the puncture and blood vessel until resistance is felt. Resistance to the proximal movement of the measuring device is caused by contact between the expandable member 28 and the wall of the blood vessel adjacent to the puncture. Additionally, the proper positioning of the expandable member 28 against the wall of the blood vessel will also be typically indicated by the cessation of blood flow through the puncture as the expandable member blocks the flow of blood from the blood vessel into the puncture. The user may then observe and record the appropriate markings along the body portion which are adjacent to proximal end of the access or procedure sheath for use in selecting the appropriate length of the medical device to be used later. Alternately, if no access or procedure sheath is used, the user may observe and record the appropriate markings along the body portion of the measuring device which are adjacent to the skin of the patient.

As described above, the appropriate catheter, sealing device, vessel plug or other medical device may now be selected and used. For example, a sealing device may then be used to seal the puncture in the manner described in the patent applications referenced above. Alternately, a procedure sheath may be moved distally along the measuring device into contact with the expandable member 28 so as to accurately position the distal end thereof adjacent to the wall of the blood vessel or target organ. In a preferred use of the present invention, the measuring device is not used until the initial medical procedure, such as angioplasty, angiography or stent placement has been performed so that the measurement step is conducted immediately prior to the sealing of the incision. This sequence of steps will preferably lessen the likelihood that a prior measurement will be misplaced or not performed prior to the initial medical procedure.

As shown in FIGS. 8–13, an alternate form of the measuring device 10 of the present invention generally consists of a semi-rigid and elongate tubular body portion 18 having a proximal end portion 20 and a distal end portion 22. The proximal end portion 20 preferably includes an actuation member 38, such as a squeeze bulb which is in fluid communication with the proximal end portion 20 via a preferably fluid containing lumen 40 which extends through the body portion 18 of the measuring device. The distal end portion 22 of the measuring device is preferably fixedly connected to the remainder of the measuring device and is slightly rounded to allow for the atraumatic insertion thereof and includes a radially expandable member 42 thereon. The expandable member 42 is preferably a balloon-type member which is in fluid communication with the actuation member 38 via the lumen 40 such that compression of the actuation member 38 on the proximal end portion 20 of the measuring device increases the fluid pressure in the lumen 40 and causes the expansion of the expandable member 42 on the distal end portion 22 of the measuring device.

As with the preferred embodiment of the present invention, the expanded size of the expandable member 42 is preferably chosen so as to not block blood flow through the blood vessel while in the expanded condition but is sufficient to provide the user with reliable tactile feedback that the expandable member 42 has contacted the wall of the blood vessel adjacent to the puncture. Additionally, the size of the expanded expandable member 42 is preferably sufficient to block the flow of blood from the blood vessel into the puncture once the expandable member is positioned in the desired location adjacent to the wall of the blood vessel and puncture. The body portion 18 is preferably formed of a semi rigid material which is opaque or transparent and includes spaced apart markings 30 thereon. The lumen 40 is preferably as small as possible while still allowing reliable fluid communication between the actuation member 38 and the expandable member 42. The diameter of the body portion is also chosen so as to conform to the diameter restrictions imposed by the intended size of the puncture and the procedure sheath used during the prior medical procedure.

As with the preferred embodiment, FIGS. 8 and 9 of the present embodiment are illustrative of the markings 30 which are printed or otherwise embossed on the outer surface of the body portion. The markings 30 begin proximally of the expandable member 42 to provide the user with an indication of the depth of the puncture relative to the interface of the proximal side of the expandable member 42 and the body portion 18. As shown, the markings 30 are preferably evenly spaced apart along the body portion 18 and may include colored bands, numbers or other readily observable indicators of the relative depth of the puncture.

Alternately, the markings may be used to identify the minimum and maximum skin depths that may be used with the specified sealing device. Therefore, as long as the skin depth is between the two markings, the desired sealing device may be used. If the skin depth is outside of the minimum and maximum skin depth markings, another size sealing device or another method of sealing may be used.

In accordance with another alternate embodiment of the present invention as shown in FIGS. 14–17, a modified measuring device 50 is shown in the drawings. Like numbers have been added to like elements described above with respect to the measuring device 10. In this embodiment, the measuring device 50 preferably includes a second lumen 52 which extends lengthwise through the proximal end portion, body portion and distal end portion of the measuring device. The diameter of the second lumen 52 is chosen to be equivalent to the outer diameter of a standard guidewire 54 so that the measuring device 50 may be inserted into the puncture over the guidewire using a seldinger type of insertion technique. In this embodiment, the guidewire may remain in the second lumen 52 during the measurement step to prevent blood from flowing through the second lumen as the measuring device 50 is positioned in the puncture. The flexibility of the body portion 18 of the measuring device 50 enables the user to slide the measuring device 50 down the guidewire through the puncture and into the blood vessel without kinking the body portion 18.

This alternate embodiment of the measuring device 50 is then used in the same manner as described above for the preferred embodiment of the measuring device 10. At the end of the measuring step, the user may observe and record the indicated depth and then either remove the measuring device 50 individually or in combination with the guidewire 54, depending on the requirements of the sealing or other device which is to be used next.

Figure 18:
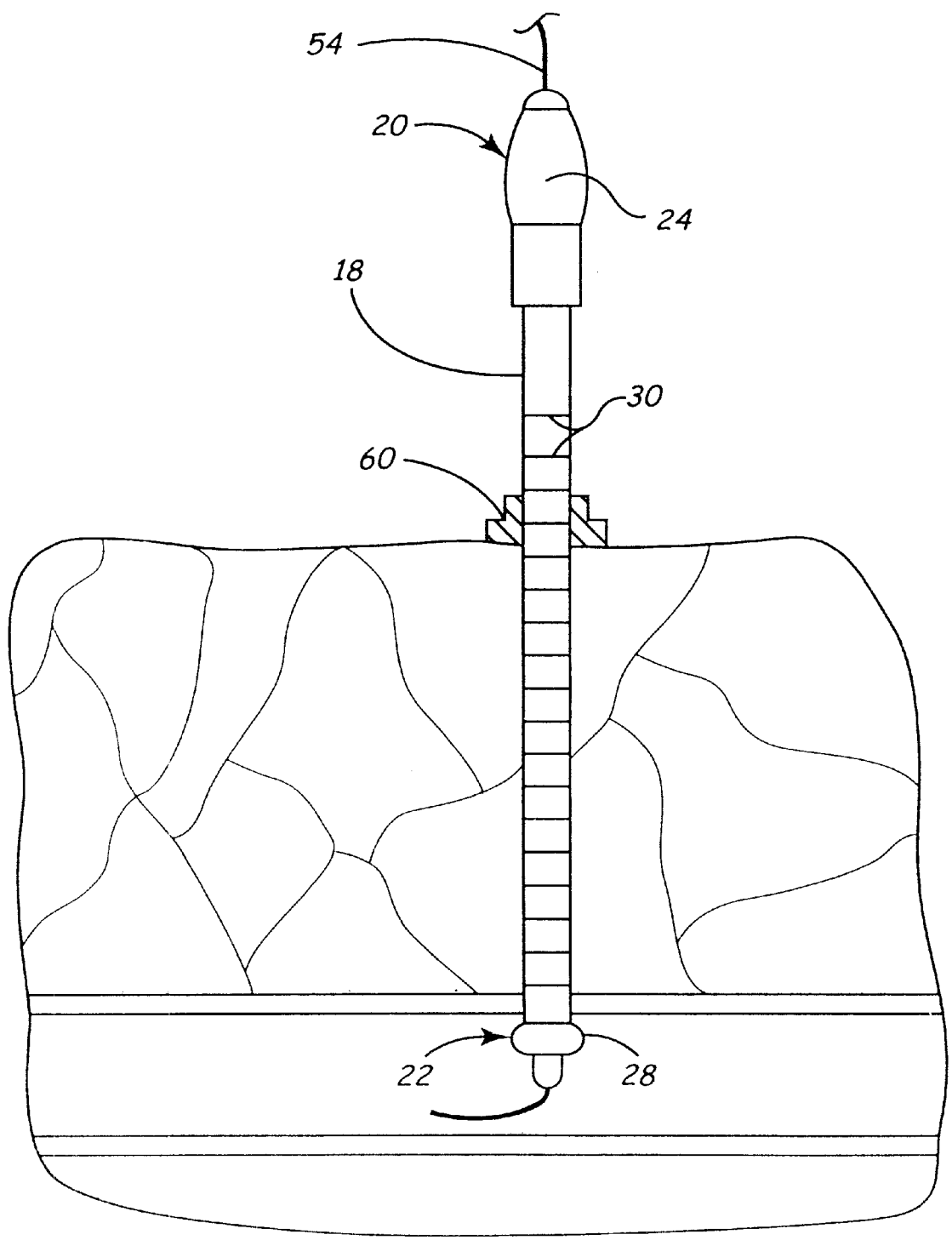
FIG. 18 is a partially elevated side view showing an alternate form of the present invention having a slidable marking member thereon and positioned in a puncture.

FIG. 18 is illustrative of a further feature or member which may be used in combination with the measuring devices described above or in a modified measuring device which does not include the outer markings 30 referred to above. In the measuring device shown in FIG. 18, a slidable member 60 may be positioned along the outer circumference of the measuring device and the measuring steps may be performed in the same manner as described above. Once the expandable member is in contact with the wall of the blood vessel adjacent to the puncture, the slidable member may be moved distally along the body portion until the slidable member 60 contacts the skin of the patient. The measuring device may then be removed from the puncture in the manner described above. Next, the user may place the measuring device having the slidable member 60 thereon along side a chart or the sealing device to determine the appropriate size sealing device. Additionally, in situations where the measuring device does not include markings, the user may place the measuring device next to the sealing device and mark the desired depth on the introducer of the sealing device so that the actual measured depth is indicated on the sealing device prior to use. This method of use enables the user to physically mark the desired depth on the sealing device prior to use of the sealing device in the event that the measured depth of the puncture does not suitably match the available sizes of the sealing devices or does not provide the user with the desired precision in the available lengths of the sealing device.

While the preferred forms of the present invention are described and illustrated herein, it will be obvious to those skilled in the art that various changes and modifications may be made thereto without departing from the scope of the present invention as defined by the following claims.

What is claimed is:

1. A device for measuring the depth below skin level of a target organ or blood vessel of a human patient that has been punctured in the course of a medical procedure, said device comprising;

an elongate tubular member having a proximal end portion, a distal end portion and a body portion therebetween, said tubular member further including a lumen extending between said proximal end portion and said distal end portion and extending through said body portion;

an elastically deformable actuation member associated with said proximal end portion of said tubular member and in communication with said lumen;

an expandable member associated with said distal end portion of said tubular member and in communication with said lumen such that actuation of said elastically deformable actuation member causes expansion of said expandable member; and a plurality of markings on said body portion which are indicative of the depth of the expandable member below the skin of the patient.

2. The device of claim 1 wherein said lumen is in fluid communication with said elastically deformable actuation member and said expandable member.

3. The device of claim 1 wherein said markings are graduated to provide a user of said device with a numerical indication of the depth of the expandable member below the skin of the patient.

4. The device of claim 1 wherein said markings are bands which correspond to the length of at least a portion of a medical device which is to be used for a subsequent medical procedure.

5. The device of claim 1 wherein said markings extend proximally from said distal end portion of said tubular member and said markings correspond to a kit for use in a subsequent medical procedure wherein the flow of fluid through the puncture is to be discontinued.

6. The device of claim 1 wherein a second lumen is in fluid communication with said distal end portion of said tubular member.

7. The device of claim 6 wherein said second lumen is sized for the receipt of a guidewire therethrough and said second lumen extends proximally from said distal end portion of said tubular member.

8. A device for measuring the depth below skin level of a target organ or blood vessel of a human patient that has been punctured in the course of a medical procedure, said device comprising;
an elongate tubular member having a proximal end portion, a distal end portion and a body portion therebetween, said tubular member further including a lumen extending between said proximal end portion and said distal end portion and extending through said body portion;
an elastically deformable actuation member associated with said proximal end portion of said tubular member and in communication with said lumen;
an expandable member associated with said distal end portion of said tubular member and in communication with said lumen such that actuation of said elastically deformable actuation member causes said distal end portion to be proximally displaced and expansion of said expandable member; and
a slidable member which is slidable along said body portion and which is movable to a position along said body portion which is indicative of the depth below the skin of the patient of the expandable member.

9. The device of claim 8 further including a plurality of graduated markings on said body portion.

10. The device of claim 8 wherein a second lumen is in communication with said distal end portion of said tubular member and extends through at least a portion of said body portion of said tubular member.

11. The device of claim 10 wherein said second lumen is sized for the receipt of a guidewire therethrough and said second lumen extends proximally from said distal end portion of said tubular member.

12. The device of claim 10 wherein said second lumen extends proximally from said distal end portion of said tubular member and through said body portion to an opening which is generally adjacent to said proximal end portion of said tubular member.

13. A device for measuring the depth below skin level of a target organ or blood vessel of a human patient that has been punctured in the course of a medical procedure, said device comprising;
an elongate tubular member having a proximal end portion, a distal end portion and a body portion therebetween, said tubular member further including a lumen extending between said proximal end portion and said distal end portion and extending through said body portion;
an elastically deformable actuation member associated with said proximal end portion of said tubular member and in communication with said lumen;
an expandable member associated with said distal end portion of said tubular member and in communication with said lumen such that actuation of said elastically deformable actuation member causes expansion of said expandable member;
said lumen being in fluid communication with said elastically deformable actuation member and said expandable member; and
a plurality of markings on said body portion which are indicative of the relative distance between the expandable member and the skin of the patient.

14. The device of claim 13 wherein a second lumen is in communication with said distal end portion of said tubular member and extends through at least a portion of said body portion of said tubular member.

15. The device of claim 14 wherein said second lumen is sized for the receipt of a guidewire therethrough and said second lumen extends proximally from said distal end portion of said tubular member.

16. A method for measuring the depth below skin level of a blood vessel of a human patient that has been punctured during the course of a medical procedure, the method comprising the steps of:
inserting a guidewire through the puncture into the blood vessel;
passing a measuring device over the guidewire wherein the measuring device has a distal end portion, a proximal end portion and a body portion wherein the distal end portion has an expandable member thereon which is in communication with an elastically deformable actuation member on the proximal end portion thereof via a lumen which extends therebetween;
advancing the measuring device over the guidewire until the distal end portion of the measuring device is positioned in the blood vessel;
actuating the elastically deformable actuation member on the proximal end portion of the measuring device to cause the expansion of the expandable member on the distal end portion of the measuring device;
withdrawing the expandable member in the blood vessel and puncture until resistance is felt due to contact between the expanded expandable member and the wall of the blood vessel; and
noting the skin level position of the measuring device relative to the expandable member.

17. The method of claim 16 wherein the skin level position of the measuring device is noted by observing graduated markings on the body portion of the measuring device.

18. The method of claim 16 wherein the skin level position of the measuring device is noted by sliding a slidable member along the body portion of the measuring device to identify the skin level position of the patient relative to the expandable member.

19. A method for measuring the depth below skin level of a blood vessel of a human patient that has been punctured during the course of a medical procedure, the method comprising the steps of:

inserting a measuring device into the puncture wherein the measuring device has a distal end portion, a proximal end portion and a body portion wherein the distal end portion has an expandable member thereon which is in communication with an elastically deformable actuation member on the proximal end portion thereof via a lumen which extends therebetween;

advancing the measuring device distally in the puncture until the distal end portion of the measuring device is positioned in the blood vessel;

actuating the elastically deformable actuation member on the proximal end portion of the measuring device to cause the distal end portion to be proximally displaced and expansion of the expandable member on the distal end portion of the measuring device;

withdrawing the expandable member in the blood vessel and puncture until resistance is felt due to contact between the expanded expandable member and the wall of the blood vessel; and noting the skin level position of the measuring device relative to the expandable member based on markings located on the body portion of the measuring device.

20. The method of claim 19 wherein the skin level position of the measuring device is noted by sliding a slidable member along the body portion of the measuring device to identify the skin level position of the patient relative to the expandable member.

* * * * *